(12) United States Patent
Orzel et al.

(10) Patent No.: US 6,453,663 B1
(45) Date of Patent: Sep. 24, 2002

(54) NOX SENSOR MONITORING

(75) Inventors: Daniel V. Orzel, Westland, MI (US); Michele T. Reichenbach, Troy, MI (US); Timothy Joseph Clark, Livonia, MI (US); William Najib Mansur, Sterling Heights, MI (US)

(73) Assignee: Ford Global Technologies, Inc, Dearborn, MI (US)

( * ) Notice: Subject to any disclaimer, the term of this patent is extended or adjusted under 35 U.S.C. 154(b) by 0 days.

(21) Appl. No.: 09/682,296

(22) Filed: Aug. 16, 2001

(51) Int. Cl.$^7$ ................................. F01N 3/00
(52) U.S. Cl. ................ 60/277; 60/274; 60/276; 123/690
(58) Field of Search ............... 60/274, 276, 277, 60/285, 297; 123/688, 690

(56) References Cited

U.S. PATENT DOCUMENTS

| 5,426,934 | A | | 6/1995 | Hunt et al. |
| 5,557,933 | A | * | 9/1996 | Numata et al. ............ 60/274 |
| 5,577,382 | A | | 11/1996 | Kihara et al. |
| 5,577,488 | A | * | 11/1996 | Sato et al. ............... 123/688 |
| 5,743,085 | A | * | 4/1998 | Takaku et al. ............. 60/276 |
| 5,927,260 | A | * | 7/1999 | Kishimoto et al. ......... 123/688 |
| 5,953,907 | A | | 9/1999 | Kato et al. |
| 5,966,930 | A | * | 10/1999 | Hatano et al. ............. 60/276 |
| 6,012,282 | A | | 1/2000 | Kato et al. |
| 6,059,947 | A | | 5/2000 | Kato et al. |
| 6,082,101 | A | * | 7/2000 | Manaka et al. ............. 60/285 |
| 6,134,883 | A | | 10/2000 | Kato et al. |
| 6,167,695 | B1 | | 1/2002 | Itou et al. |
| 2001/0002550 | A1 | | 6/2001 | Zhang et al. |

* cited by examiner

Primary Examiner—Thomas Denion
Assistant Examiner—Binh Tran
(74) Attorney, Agent, or Firm—Julia Voutyras; Allan Lippa

(57) ABSTRACT

A method for determining deterioration of an exhaust gas sensor coupled downstream of an emission control device by monitoring the sensor's response to a change in an air-fuel ratio is presented. In particular, the sensor is monitored for a predetermined time period following a switch from lean to rich operation and a ratio of a maximum and minimum value is determined. The ratio is then compared to a threshold value to evaluate sensor performance. This method achieves improved emission control and fuel economy.

11 Claims, 3 Drawing Sheets

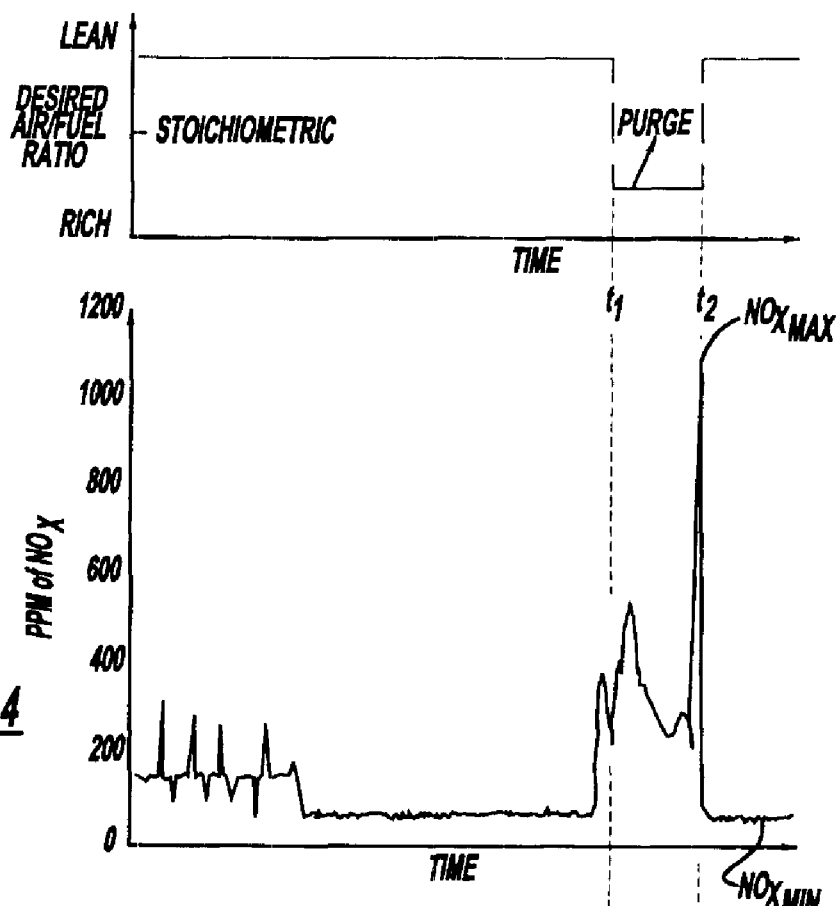
*Figure - 3*
*Figure - 4*
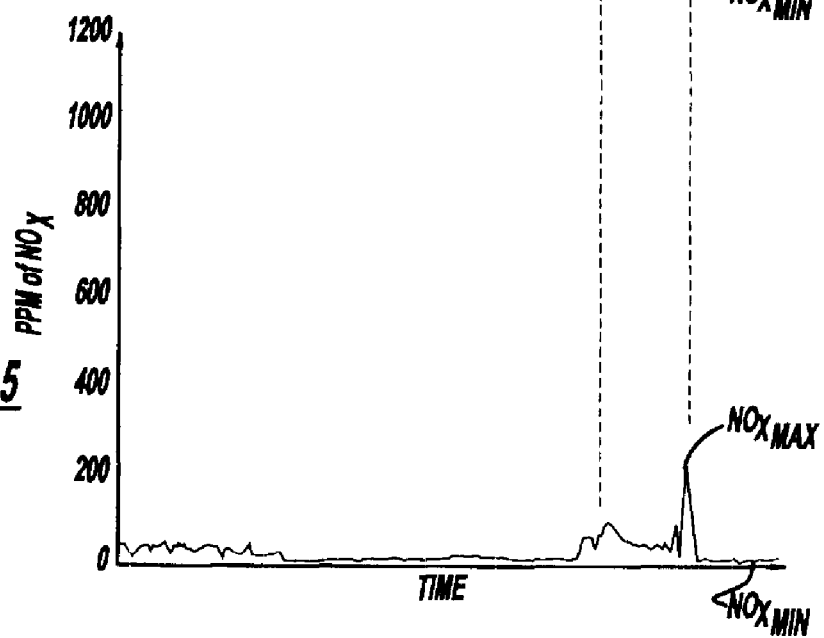
*Figure - 5*

NOX SENSOR MONITORING

BACKGROUND OF INVENTION

The present invention relates to a system and a method for monitoring an engine emission control system, and in particular to monitoring a NOx sensor coupled downstream of an emission control device.

Internal combustion engines are typically coupled to an emission control device known as a three-way catalytic converter (TWC) designed to reduce combustion by-products such as carbon monoxide (CO), hydrocarbon (HC) and oxides of nitrogen (NOx). Engines can operate at air-fuel mixture ratios lean of stoichiometry, thus improving fuel economy. For lean engine operation, an additional three-way catalyst commonly referred to as a Lean NOx Trap (LNT), is usually coupled downstream of an upstream catalytic converter. The LNT stores exhaust components, such as oxygen and NOx, during lean operation. Continued lean operation eventually saturates the LNT with the selected exhaust gas constituents. After the LNT is filled to a predetermined capacity, stored exhaust gas constituents are typically reduced and released (purged) by switching to rich or stoichiometric operation, i.e., by increasing the ratio of fuel to air and thereby increasing the amount of reductant such as hydrocarbon (HC) present in the exhaust gas mixture entering the LNT. Once the purge is completed, lean operation resumes again.

One way of determining when to purge the LNT is by installing a sensor capable of measuring an amount of NOx in the exhaust gas exiting the LNT. Typically, the sensor is monitored to determine when the amount of tailpipe NOx emissions in grams/mile exceeds a predetermined threshold in order to discontinue lean operation. Over time, the performance of the NOx sensor can deteriorate due to such causes as contamination or electrical degradation. This can result in an incorrect determination of when to end lean operation, and may result in lean operation being too long or too short, thus degrading emission control or fuel economy. It is therefore desirable to monitor the performance of the emission control system, and in particular to detect the degradation of the NOx sensor.

One method of NOx sensor monitoring is described in U.S. Pat. No. 5,426,934, wherein a NOx catalyst is coupled to an upstream (post-catalyst) and a downstream (pre-catalyst) NOx sensor. Only the upstream (pre-catalyst) NOx sensor is monitored for deterioration. The method includes comparing the ratio of the NOx sensor output during lean operation ($NO_{xlean}$) and the NOx sensor output at stoichiometry ($NO_{xrich}$) to a predetermined value. A decrease in the ratio below the predetermined value is indicative of sensor deterioration.

The inventors herein have recognized a disadvantage with this approach. Namely, this method would not work for a post-catalyst NOx sensor since the LNT stores NOx during lean operation, and therefore the $NO_{xlean}$ signal downstream of the LNT will be attenuated. Therefore, the ratio of the prior art cannot be used as an indicator of post-catalyst sensor deterioration.

SUMMARY OF INVENTION

It is an object of the present invention to provide a system and a method for determining degradation in an emission control system.

In carrying out the above object and other objects, features and advantages of the present invention, a system and a method for determining degradation in an emission control system comprising an exhaust gas aftertreatment device having a downstream sensor coupled to it, include: changing an air-fuel mixture of an exhaust gas entering the device; and determining degradation of the sensor based on a response of the sensor to said change in said air-fuel ratio.

For example, in accordance with one embodiment of the present invention, the inventors have recognized that once lean operation is discontinued, and the air-fuel ratio of the exhaust gas entering the LNT is switched to rich, there is a significant temporary increase in the amount of NOx in the exhaust gas exiting the LNT, which is typically reflected by a surge in the NOx sensor output if the NOx sensor is not degraded. Further, the inventors have recognized that a degraded sensor will not detect this surge in the amount of NOx exiting the LNT. The NOx surge can occur within a predetermined time period following the lean to rich transition, and may sometimes happen after the purge is completed, and the air-fuel ratio is changed back to lean. It is partially due to a significant temperature increase of the LNT resulting from the increased amount of reductant entering it during the purge. In other words, increased LNT temperature contributes to increased NOx in the exhaust gas exiting the LNT. Therefore, under the present invention, the performance of the NOx sensor can be monitored by monitoring its response to the NOx surge for a predetermined time period following the switch from lean to rich operation.

In accordance with another feature of the present invention, in an exemplar embodiment, a system and a method for determining degradation in an emission control system comprising an exhaust gas aftertreatment device having a downstream sensor coupled to it, include: operating the engine at an air-fuel ratio lean of stoichiometry to store an exhaust gas constituent in the device; temporarily switching to an air-fuel ratio rich of stoichiometry to release said stored exhaust gas constituent from the device; reading an output of the sensor for a predetermined period following said temporary switch to determine a maximum value and a minimum value of said reading; and comparing a ratio of said maximum value and said minimum value to a predetermined threshold.

Therefore, according to this embodiment, it is possible to detect deterioration in the sensor by determining a maximum and a minimum value of the sensor reading following a switch to rich mode of operation, and by comparing the ratio of the two to a predetermined threshold indicative of a borderline sensor performance. In other words, a sensor that is not deteriorated will detect a surge in the amount of NOx exiting the LNT in response to a switch to rich operation, and the ratio of the maximum value to a minimum value taken during a predetermined period following the switch will be above a threshold amount. On the other hand, a deteriorated sensor will not detect the surge, and the ratio of maximum to minimum value will be below a predetermined threshold.

An advantage of the above aspects of invention is optimized lean running time, increased fuel economy, and improved emission control.

The above advantages and other advantages, objects and features of the present invention will be readily apparent from the following detailed description of the preferred embodiments when taken in connection with the accompanying drawings.

BRIEF DESCRIPTION OF DRAWINGS

The objects and advantages described herein will be more fully understood by reading an example of an embodiment in which the invention is used to advantage, referred to herein as the Description of Preferred Embodiment, with reference to the drawings, wherein:

FIG. 3 depicts the desired engine air-fuel ratio versus time;

FIG. 4 depicts outputs of a non-deteriorated NOx sensor versus time in response to a change in air-fuel ratio; and FIG. 5 depicts outputs of a deteriorated NOx sensor versus time in response to a change in air-fuel ratio.

DETAILED DESCRIPTION

As will be appreciated by those of ordinary skill in the art, the present invention is independent of the particular underlying engine technology and configuration. As such, the present invention may be used in a variety of types of internal combustion engines, such as conventional engines, in addition to direct injection stratified charge (DISC) or direct injection spark ignition engines (DISI).

Figure 1:
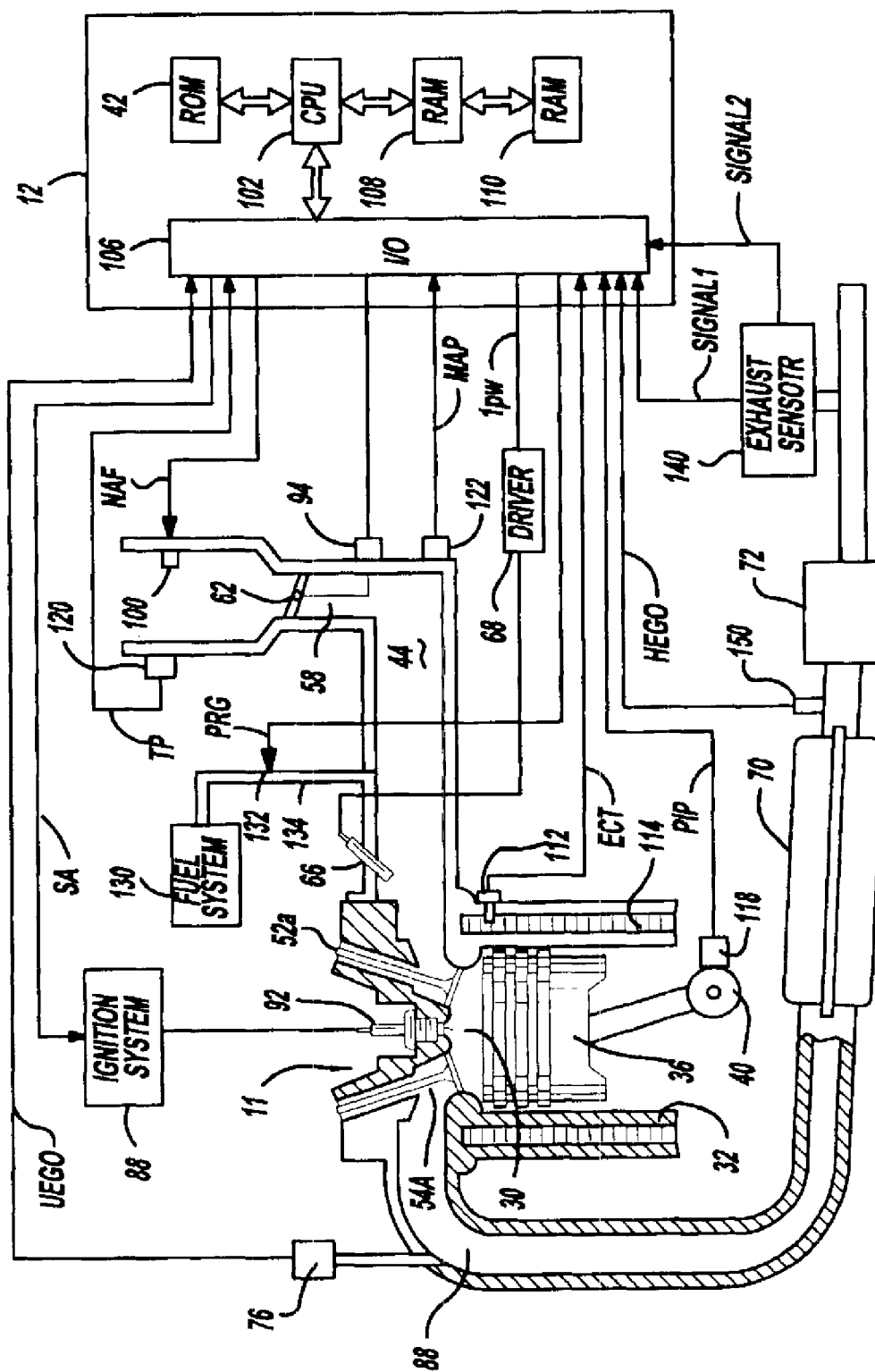
FIG. 1 is a block diagram of an internal combustion engine illustrating various components related to the present invention.

A block diagram illustrating an engine control system and method for a representative internal combustion engine according to the present invention is shown in FIG. 1. Preferably, such an engine includes a plurality of combustion chambers, only one of which is shown, and is controlled by electronic engine controller 12. Combustion chamber 30 of engine 10 includes combustion chamber walls 32 with piston 36 positioned therein and connected to crankshaft 40. In this particular example, the piston 30 includes a recess or bowl (not shown) for forming stratified charges of air and fuel. In addition, combustion chamber 30 is shown communicating with intake manifold 44 and exhaust manifold 48 via respective intake valves 52a and 52b (not shown), and exhaust valves 54a and 54b (not shown). A fuel injector 66 is shown directly coupled to combustion chamber 30 for delivering liquid fuel directly therein in proportion to the pulse width of signal fpw received from controller 12 via conventional electronic driver 68. Fuel is delivered to the fuel injector 66 by a conventional high-pressure fuel system (not shown) including a fuel tank, fuel pumps, and a fuel rail.

Intake manifold 44 is shown communicating with throttle body 58 via throttle plate 62. In this particular example, the throttle plate 62 is coupled to electric motor 94 such that the position of the throttle plate 62 is controlled by controller 12 via electric motor 94. This configuration is commonly referred to as electronic throttle control, (ETC), which is also utilized during idle speed control. In an alternative embodiment (not shown), which is well known to those skilled in the art, a bypass air passageway is arranged in parallel with throttle plate 62 to control inducted airflow during idle speed control via a throttle control valve positioned within the air passageway.

Exhaust gas sensor 76 is shown coupled to exhaust manifold 48 upstream of catalytic converter 70. In this particular example, sensor 76 is a universal exhaust gas oxygen (UEGO) sensor, also known as a proportional oxygen sensor. The UEGO sensor generates a signal whose magnitude is proportional to the oxygen level (and the air-fuel ratio) in the exhaust gases. This signal is provided to controller 12, which converts it into a relative air-fuel ratio. Advantageously, signal UEGO is used during feedback air-fuel ratio control in to maintain average air-fuel ratio at a desired air-fuel ratio as described later herein. In an alternative embodiment, sensor 76 can provide signal EGO, exhaust gas oxygen (not shown), which indicates whether exhaust air-fuel ratio is lean or rich of stoichiometry. In another alternate embodiment, the sensor 76 may comprise one of a carbon monoxide (CO) sensor, a hydrocarbon (HC) sensor, and a NOx sensor that generates a signal whose magnitude is related to the level of CO, HC, NOx, respectively, in the exhaust gases. Those skilled in the art will recognize that any of the above exhaust gas sensors may be viewed as an air-fuel ratio sensor that generates a signal whose magnitude is indicative of the air-fuel ratio measured in exhaust gases.

Conventional distributorless ignition system 88 provides ignition spark to combustion chamber 30 via spark plug 92 in response to spark advance signal SA from controller 12.

Controller 12 causes combustion chamber 30 to operate in either a homogeneous air-fuel ratio mode or a stratified air-fuel ratio mode by controlling injection timing. In the stratified mode, controller 12 activates fuel injector 66 during the engine compression stroke so that fuel is sprayed directly into the bowl of piston 36. Stratified air-fuel layers are thereby formed. The stratum closest to the spark plug contains a stoichiometric mixture or a mixture slightly rich of stoichiometry, and subsequent strata contain progressively leaner mixtures. In the homogeneous mode, controller 12 activates fuel injector 66 during the intake stroke so that a substantially homogeneous air-fuel mixture is formed when ignition power is supplied to spark plug 92 by ignition system 88. Controller 12 controls the amount of fuel delivered by fuel injector 66 so that the homogeneous air-fuel ratio mixture in chamber 30 can be selected to be substantially at (or near) stoichiometry, a value rich of stoichiometry, or a value lean of stoichiometry. Operation substantially at (or near) stoichiometry refers to conventional closed loop oscillatory control about stoichiometry. The stratified air-fuel ratio mixture will always be at a value lean of stoichiometry, the exact air-fuel ratio being a function of the amount of fuel delivered to combustion chamber 30.

An additional split mode of operation, wherein additional fuel is injected during the exhaust stroke while operating in the stratified mode, is available. An additional split mode of operation wherein additional fuel is injected during the intake stroke while operating in the stratified mode is also available, where a combined homogeneous and split mode is available.

Lean NOx Trap 72 is shown positioned downstream of catalytic converter 70. Both devices store exhaust gas components, such as $NO_X$ and oxidants, when engine 10 is operating lean of stoichiometry. The stored exhaust gas components are subsequently reacted with HC and other reductant and are catalyzed during a purge cycle when controller 12 causes engine 10 to operate in either a rich mode or a near Exhaust gas oxygen sensor 150 also known as a catalyst monitoring sensor (CMS) is shown coupled to exhaust manifold 48 between the catalytic converter 70 and the NOx trap 72. In this particular example, sensor 150 provides signal HEGO to controller 12, and essentially serves as a switch providing information as to whether the air-fuel mixture is lean or rich at the mid-bed location.

Controller 12 is shown in FIG. 1 as a conventional microcomputer including but not limited to: microprocessor unit 102, input/output ports 104, an electronic storage medium for executable programs and calibration values, shown as read-only memory chip 106 in this particular example, random access memory 108, keep alive memory 110, and a conventional data bus.

Controller 12 is shown receiving various signals from sensors coupled to engine 10, in addition to those signals previously discussed, including: measurement of inducted mass air flow (MAF) from mass air flow sensor 100 coupled to throttle body 58; engine coolant temperature (ECT) from temperature sensor 112 coupled to cooling sleeve 114; a profile ignition pickup signal (PIP) from Hall effect sensor 118 coupled to crankshaft 40 giving an indication of engine speed (RPM); throttle position TP from throttle position sensor 120; and absolute Manifold Pressure Signal MAP from sensor 122. Engine speed signal RPM is generated by controller 12 from signal PIP in a conventional manner and manifold pressure signal MAP provides an indication of engine load.

Fuel system 130 is coupled to intake manifold 44 via tube 132. Fuel vapors (not shown) generated in fuel system 130 pass through tube 132 and are controlled via purge valve 134. Purge valve 134 receives control signal PRG from controller 12.

Exhaust sensor 140 is a NOx/UEGO sensor located downstream of the LNT. It produces two output signals. Both first output signal (SIGNAL1) and second output signal (SIGNAL2) are received by controller 12. Exhaust sensor 140 can be a sensor known to those skilled in the art that is capable of indicating both exhaust air-fuel ratio and nitrogen oxide concentration.

In a preferred embodiment, SIGNAL1 indicates exhaust air-fuel ratio and SIGNAL2 indicates nitrogen oxide concentration. In this embodiment, sensor 140 has a first chamber (not shown) in which exhaust gas first enters where a measurement of oxygen partial pressure is generated from a first pumping current. Also, in the first chamber, oxygen partial pressure of the exhaust gas is controlled to a predetermined level. Exhaust air-fuel ratio can then be indicated based on this first pumping current. Next, the exhaust gas enters a second chamber (not shown) where $NO_X$ is decomposed and measured by a second pumping current using the predetermined level. Nitrogen oxide concentration can then be indicated based on this second pumping current. In an alternative embodiment, a separate NOx sensor could be used in conjunction with an air-fuel sensor, which could be a UEGO or a HEGO sensor.

Figure 2:
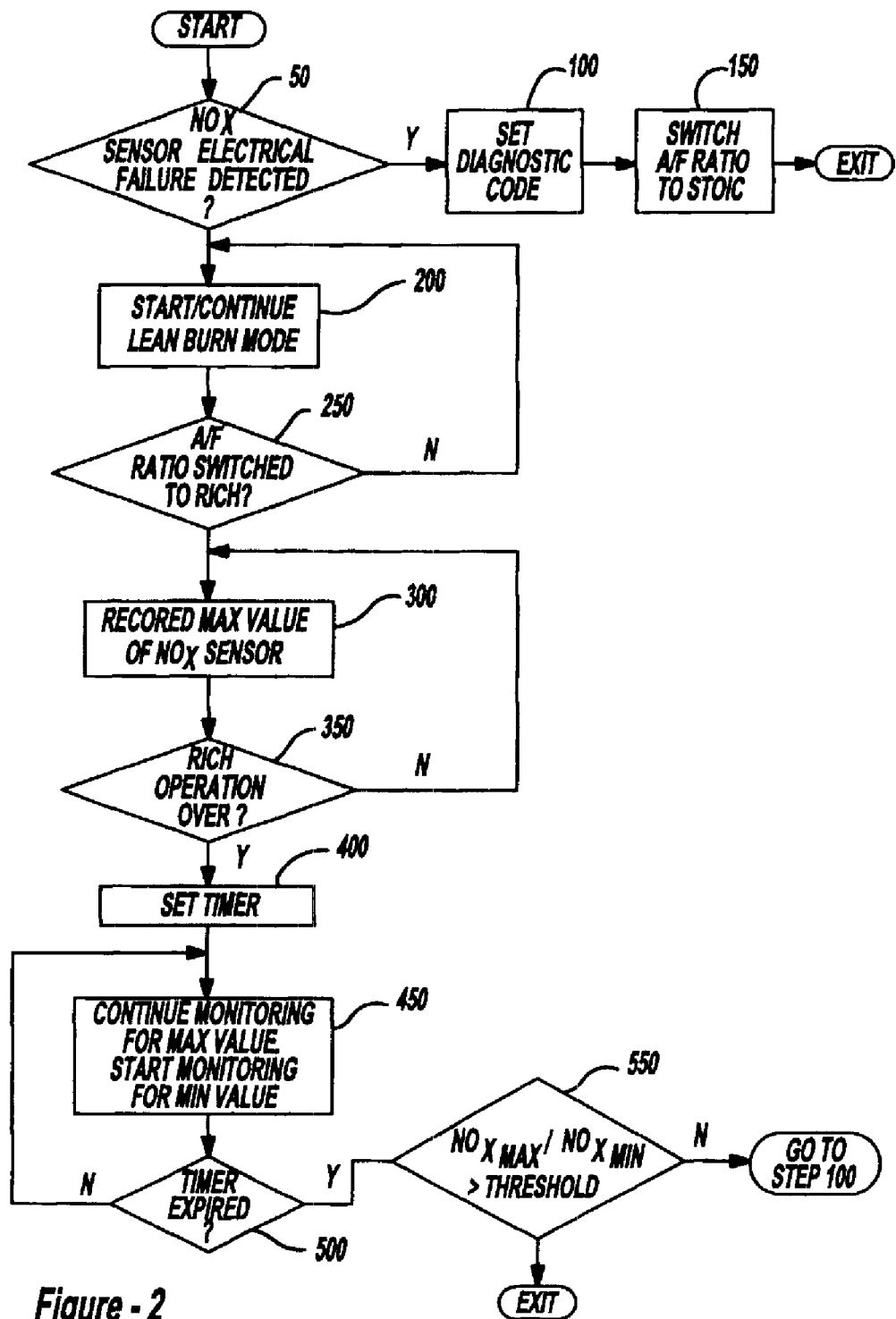
FIG. 2 is a block diagram of the embodiment in which the invention is used to advantage.

The diagram in FIG. 2 generally represents operation of one embodiment of a system or method according to the present invention. As will be appreciated by one of ordinary skill in the art, the diagram may represent one or more of any number of processing strategies such as event-driven, interrupt-driven, multi-tasking, multi-threading, and the like. As such, various steps or functions illustrated may be performed in the sequence illustrated, I parallel, or in some cases omitted. Likewise, the order of processing is not necessarily required to achieve the objects, features and advantages of the invention, but is provided for ease of illustration and description. Although not explicitly illustrated, one of ordinary skill in the art will recognize that one or more of the illustrated steps or functions may be repeatedly performed depending on the particular strategy being used.

Referring now to FIG. 2, the routine begins in step 50 wherein a determination is made whether any NOx sensor electrical failure (i.e., short to power or ground, or open circuit) has been detected. If the answer to step 50 is YES, a diagnostic code is set in step 100, and the routine proceeds to step 150 wherein engine operation is switched to stoichiometric in the absence of a properly functioning NOx sensor, and the routine exits. If the answer to step 50 is NO, the routine proceeds to step 200 wherein a lean-burn mode of operation (i.e., engine operation is at an air-fuel ratio lean of stoichiometry) commences. Next, in step 250, a determination is made whether engine operation has been switched to rich. The switch to air fuel ratio rich of stoichiometric could be due to, for example, the LNT being saturated with NOx, or to an increased demand in engine output torque. If the answer to step 250 is YES, the routine proceeds to step 300, the output of the NOx sensor (in this example, SIGNAL2 of NOx/UEGO sensor 140, as described in FIG. 1) is monitored in order to determine a maximum NOx sensor value ($NOx_{max}$) following the switch. The routine then proceeds to step 350 wherein a determination is made whether the rich operation has been discontinued, due to, for example, completion of the purge of the LNT, or decreased engine output torque demand. If the answer to step 350 is NO, i.e., rich operation has not been discontinued, the routine returns to step 300, wherein monitoring of the NOx sensor output for a maximum value continues. If the answer to step 350 is YES, i.e., rich operation is discontinued, the routine proceeds to step 400 wherein a calibratable timer is set, and then to step 450 wherein the NOx sensor output continues to be monitored for a maximum value and also monitoring for a minimum value of NOx sensor output, ($NOx_{min}$) commences. Next, in step 500, a determination is made whether the timer set in step 400 has exceeded a predetermined value. If the answer to step 500 is NO, the routine returns to step 450. If the answer to step 500 is YES, the routine proceeds to step 550 wherein a decision is made whether the ratio of $NOx_{max}/NOx_{min}$ is greater than a predetermined threshold. If the answer to step 550 is YES, sensor performance is not degraded, and the routine returns to step 100 wherein monitoring continues. If the answer to step 550 is NO, sensor performance is degraded, routine returns to step 150.

Therefore, according to the present invention, it is possible to diagnose degradation in an exhaust sensor coupled downstream of an emission control device by varying the air-fuel ratio of the exhaust gas mixture entering the device and comparing the response of the sensor to the change in the air-fuel ratio to a predicted response. In one of the embodiments, the response of the sensor to a switch from lean to rich air-fuel ratio is monitored by determining a ratio of a maximum and minimum sensor reading during a predetermined period following the switch and comparing the ratio to a predetermined threshold. If the sensor performance is judged degraded, the engine control strategy could be adjusted, for example, by changing the air-fuel ratio to stoic.

Proceeding now to FIG. 3, an exemplary plot of desired engine air-fuel ratio is depicted. As can be seen in the plot, at time $t_1$ the air fuel ratio is changed from lean to rich (due to, for example, driver demand for extra torque, or to the LNT being saturated with NOx). At time $t_2$, rich operation is discontinued (i.e., NOx purge is completed) and lean operation resumes.

Referring now to FIG. 4, an exemplary plot of a properly functioning NOx sensor response to changes in the desired air-fuel ratio is depicted. The $NOx_{max}/NOx_{min}$ ratio is above a threshold value which in this example is around 500 ppm.

Referring now to FIG. 5, an exemplary plot of a degraded NOx sensor response to changes in the desired air-fuel ratio is depicted. It can be seen that the $NOx_{max}/NOx_{min}$ ratio is below an exemplary 500 ppm threshold value.

This concludes the description of the invention. The reading of it by those skilled in the art would bring to mind many alterations and modifications without departing from the spirit and the scope of the invention. Accordingly, it is intended that the scope of the invention is defined by the following claims:

What is claimed is:

1. A method for determining degradation in an emission control system comprising an exhaust gas aftertreatment device the system coupled downstream of an internal combustion engine, the method comprising:

operating the engine at an air-fuel ratio lean of stoichiometry to store an exhaust gas constituent in the device;

temporarily switching to an air-fuel ratio rich of stoichiometry to release said exhaust gas constituent from the device;

reading an output of a NOx sensor coupled downstream of the device for a predetermined period following said temporary switch to determine a maximum value and a minimum value of said reading; and comparing a ratio of said maximum value and said minimum value to a predetermined threshold.

2. The method cited in claim 1 wherein the exhaust gas aftertreatment device is a three-way catalyst.

3. The method cited in claim 1 wherein said predetermined period is a time period.

4. The method cited in claim 1 further comprising making a determination of sensor degradation based on said comparison.

5. The method cited in claim 4 further comprising switching engine operation to stoichiometric in response to said determination of degradation.

6. The method as set forth in claim 1 wherein the device is a Lean NOx trap.

7. A system for detecting degradation in an emission control system coupled downstream of an internal combustion engine, the system comprising:

an exhaust gas aftertreatment device;

a Nox sensor coupled downstream of said device; and a controller changing an air-fuel ratio of an exhaust gas mixture entering said device, said controller detecting degradation of said NOx sensor based on a comparison of a ratio of a maximum value and a minimum value of a response of said sensor to said air-fuel ratio change to a threshold value.

8. The system cited in claim 7 wherein said exhaust gas aftertreatment device is a three-way catalyst.

9. The system cited in claim 7 wherein said controller changes said air-fuel ratio from lean to rich.

10. The system cited in claim 7 wherein said controller changes said air-fuel ratio from rich to lean.

11. The method as set forth in claim 7 wherein said exhaust gas aftertreatment device is a Lean NOx trap.

* * * * *